(12) United States Patent
Nave et al.

(10) Patent No.: US 10,478,054 B2
(45) Date of Patent: Nov. 19, 2019

(54) ENDOTRACHEAL TUBE WITH VISUALIZATION CAPABILITIES AND A LARYNGEAL MASK

(71) Applicant: ETVIEW Ltd., Misgav (IL)

(72) Inventors: Omri Nave, Misgav (IL); William Edelman, Sharon, MA (US)

(73) Assignee: AMBU A/S, Ballerup (DK)

( * ) Notice: Subject to any disclaimer, the term of this patent is extended or adjusted under 35 U.S.C. 154(b) by 276 days.

(21) Appl. No.: 15/431,675

(22) Filed: Feb. 13, 2017

(65) Prior Publication Data

US 2017/0232216 A1    Aug. 17, 2017

Related U.S. Application Data

(60) Provisional application No. 62/294,320, filed on Feb. 12, 2016.

(51) Int. Cl.
| | |
|---|---|
| *A61B 1/06* | (2006.01) |
| *A61B 1/267* | (2006.01) |
| *A61B 1/012* | (2006.01) |
| *A61B 1/12* | (2006.01) |
| *A61B 1/00* | (2006.01) |
| *A61M 16/04* | (2006.01) |
| *A61M 16/08* | (2006.01) |

(52) U.S. Cl.
CPC ........ *A61B 1/0676* (2013.01); *A61B 1/00119* (2013.01); *A61B 1/00135* (2013.01); *A61B 1/012* (2013.01); *A61B 1/12* (2013.01); *A61B 1/126* (2013.01); *A61B 1/267* (2013.01)

(58) Field of Classification Search
CPC ... A61B 1/0676; A61B 1/267; A61B 1/00119; A61B 1/00135; A61B 1/012; A61B 1/12; A61B 1/126; A61M 16/04; A61M 16/0409; A61M 16/0434; A61M 16/0445; A61M 16/0484; A61M 16/0486
See application file for complete search history.

(56) References Cited

U.S. PATENT DOCUMENTS

| | | | |
|---|---|---|---|
| 4,437,458 | A | 3/1984 | Upsher |
| 4,509,514 | A | 4/1985 | Brain |
| 5,241,956 | A | 9/1993 | Brain |
| 5,282,464 | A | 2/1994 | Brain |
| 5,297,547 | A | 3/1994 | Brain |
| 5,499,625 | A | 3/1996 | Frass et al. |

(Continued)

FOREIGN PATENT DOCUMENTS

| | | |
|---|---|---|
| WO | WO 97/37709 | 10/1997 |
| WO | WO 99/45990 | 9/1999 |

(Continued)

*Primary Examiner* — Aaron B Fairchild
(74) *Attorney, Agent, or Firm* — Faegre Baker Daniels LLP (57) ABSTRACT

A method for intubation of a patient comprising: providing an LMA and an endotracheal tube, wherein the endotracheal tube comprises a visualization device and wherein the endotracheal tube is adapted for passing through the LMA; positioning the LMA in the patient; and guiding the endotracheal tube with the aid of the visualization device through the LMA for positioning in the trachea of the patient. The method preferably further comprises removing the LMA from the patient following the positioning of the endotracheal tube while leaving the endotracheal tube in position.

8 Claims, 11 Drawing Sheets

(56) References Cited

U.S. PATENT DOCUMENTS

| | | |
|---|---|---|
| 5,623,921 A | 4/1997 | Kinsinger et al. |
| 5,913,816 A | 6/1999 | Sanders et al. |
| 5,941,816 A | 8/1999 | Barthel et al. |
| 6,079,409 A * | 6/2000 | Brain ............... A61M 16/0409 128/200.26 |
| 6,189,533 B1 | 2/2001 | Simon et al. |
| 7,052,456 B2 | 5/2006 | Simon |
| 7,128,071 B2 | 10/2006 | Brain |
| 7,174,889 B2 | 2/2007 | Boedeker |
| 7,938,119 B2 | 5/2011 | Chen et al. |
| 8,479,739 B2 | 7/2013 | Hirsh |
| 8,863,746 B2 | 10/2014 | Totz |
| 9,357,905 B2 | 6/2016 | Molnar et al. |
| 9,421,341 B2 | 8/2016 | Miller |
| 9,486,595 B2 | 11/2016 | Borrye et al. |
| 9,572,946 B2 | 2/2017 | Chun |
| 9,579,012 B2 | 2/2017 | Vazales et al. |
| 9,788,755 B2 | 10/2017 | Hayman et al. |
| 9,801,535 B2 | 10/2017 | Turnbull |
| 10,245,402 B2 | 4/2019 | Daher et al. |
| 10,314,993 B2 | 6/2019 | Hansen et al. |
| 2001/0017135 A1* | 8/2001 | Cook ............... A61M 16/04 128/207.15 |
| 2001/0023312 A1 | 9/2001 | Pacey |
| 2002/0077527 A1 | 6/2002 | Aydelotte |
| 2002/0108610 A1 | 8/2002 | Kent |
| 2002/0162557 A1 | 11/2002 | Simon et al. |
| 2005/0039754 A1 | 2/2005 | Simon |
| 2005/0090712 A1 | 4/2005 | Cubb |
| 2005/0268917 A1* | 12/2005 | Boedeker ............ A61M 16/04 128/207.14 |
| 2006/0025650 A1* | 2/2006 | Gavriely ............ A61B 1/00057 600/110 |
| 2006/0180155 A1 | 8/2006 | Glassenberg |
| 2010/0249639 A1 | 9/2010 | Bhatt |
| 2011/0275894 A1* | 11/2011 | Mackin ............... A61B 1/00016 600/109 |
| 2011/0315147 A1 | 12/2011 | Wood et al. |
| 2012/0172664 A1 | 7/2012 | Hayman et al. |
| 2012/0259173 A1 | 10/2012 | Waldron et al. |
| 2012/0302833 A1 | 11/2012 | Hayman et al. |
| 2014/0046142 A1 | 2/2014 | Gavriely |
| 2014/0128672 A1* | 5/2014 | Daher ............... A61M 16/0404 600/104 |
| 2016/0101254 A1 | 4/2016 | Hansen, Jr. |
| 2016/0157708 A1 | 6/2016 | Daher |
| 2016/0206189 A1 | 7/2016 | Nearman et al. |
| 2016/0227991 A1 | 8/2016 | Hayut et al. |
| 2016/0287825 A1 | 10/2016 | Daher |

FOREIGN PATENT DOCUMENTS

| | | |
|---|---|---|
| WO | WO 2008/103448 | 8/2008 |
| WO | WO 2012/091859 | 7/2012 |

* cited by examiner

ENDOTRACHEAL TUBE WITH VISUALIZATION CAPABILITIES AND A LARYNGEAL MASK

CROSS-REFERENCE TO RELATED APPLICATIONS

This application claims the benefit of priority from commonly owned U.S. Patent Application No. 62/294,320, filed on Feb. 12, 2016, the entire disclosure of which is hereby incorporated by reference.

TECHNICAL FIELD

This disclosure relates to upper airway tubes and intubation methods. More particularly the disclosure relates to an endotracheal tube with visualization capabilities and a method of intubation with the endotracheal tube and a laryngeal mask.

BACKGROUND

An endotracheal tube may be inserted into the trachea of a patient who is in acute respiratory failure or is undergoing general anesthesia and requires artificial ventilation. The most common method of providing artificial ventilation is by pumping compressed air into the patient's lungs through the endotracheal tube. This tube is inserted through the patient's mouth or nose and passed between the vocal cords into the trachea. Alternatively, a tube may be inserted into the trachea through a tracheotomy surgical incision. The endotracheal tube must be placed quickly and accurately and positioned with its tip in the mid portion of the patient's trachea to prevent accidental slipping and to provide proper seal and ventilation of both lungs.

Once the endotracheal tube is in place it is secured to prevent inadvertent movement thereof during use to prevent accidents. The endotracheal tube may be secured by inflating a cuff that surrounds the tube near its distal tip. The inflated cuff occludes the space between the outer wall of the tube and the inner wall of the trachea to provide an airtight seal and hold the tube in place. Accidental insertion of the tube into the esophagus or placing it too deep inside the airways, so that its tip is lodged in one of the main stem bronchi instead of in the trachea, may lead to catastrophic consequences and asphyxiation of the patient.

For oral intubation an operator may use a laryngoscope, which consists of a handle and a blade. The operator inserts the blade into the patient's mouth and advances it until its tip lies in the pharynx beyond the root of the tongue. The handle is then used to manipulate the blade and push the tongue out of the way until the epiglottis and the vocal folds can be seen. The tip of the endotracheal tube can then be aimed and pushed between the vocal folds into the trachea. This method of insertion is used in the majority of intubations, but requires skill, training, and experience and is only performed by specialized physicians and licensed paramedics.

An alternative method that is often used requires a fiber optic bronchoscope. First the bronchoscope is connected to a light source to provide the needed illumination of the field facing its tip. The shaft of the bronchoscope is then inserted through the endotracheal tube and moved in as far as possible. The tip of bronchoscope is then inserted into the patient's airway and advanced under visualization, through the bronchoscope's eyepiece or a video display, in between the vocal folds into the trachea. The endotracheal tube can now be pushed down the bronchoscope's shaft and moved between the vocal folds into the trachea. The endotracheal tube can now be secured and the bronchoscope removed to free up the lumen of the endotracheal tube. While the bronchoscopic method is safer than intubation with the laryngoscope, the equipment needed is expensive, delicate, more cumbersome, and is seldom found in the field or on emergency medical vehicles.

Other methods to verify the placement of the endotracheal tube include: auscultation of both sides of the chest to verify symmetric air entry into both lungs, a chest x-ray to verify the tube placement but requiring further x-rays whenever the tube is placed or repositioned, a suction bulb, or through sending and receiving an acoustic signal.

Alternatively, a laryngeal mask airway (LMA) is used as a conduit for endotracheal tube placement. The laryngeal mask airway or laryngoscope mask is useful for establishing airways in unconscious patients. An example of an LMA is disclosed in U.S. Pat. No. 4,509,514, which is hereby incorporated by reference as if fully set forth herein. The LMA typically comprises a curved or flexible tube opening at a distal end into the interior of a hollow mask portion shaped to conform to and to fit readily into the actual and potential space behind the larynx and to seal around the circumference of the laryngeal inlet without penetrating into the interior of the larynx. The mask portion of the device may have an inflatable periphery or cuff which is adapted to form the seal around the laryngeal inlet. Alternatively or in addition, the mask portion may have an inflatable posterior part which is adapted to press against the back of the throat and thereby increase the sealing pressure around the laryngeal inlet.

Combining the use of the LMA and the endotracheal tube is advantageous as the LMA can provide initial ventilation of the patient and the endotracheal tube can be inserted at a later stage such as when the patient's oxygen level has reached a desired point. When an LMA is already in position, the endotracheal tube is fed through the LMA and the vocal folds into the trachea. Correct insertion and placement of the endotracheal tube by current methods remains cumbersome and problematic. The most common method—using a fiber optic bronchoscope as described above—is made more complex by the presence of the LMA.

There is an unmet need for, and it would be highly useful to have, a method and system that allowed for use of an LMA along with an endotracheal tube that allowed for simplified insertion and correct placement of the endotracheal tube and, optionally, removal of the LMA once the endotracheal tube was in place.

SUMMARY OF THE DISCLOSURE

The present embodiments of this disclosure overcome the deficiencies of the background by providing an endotracheal tube with visualization capabilities such as an integrated camera and light source, adapted for use with an LMA. In one example, the visualization capabilities enable a method of intubation of a patient using the endotracheal tube via an in-place LMA including guiding of the endotracheal tube to the correct position within the trachea. The endotracheal tube is further adapted to allow removal of the LMA once the endotracheal tube is secured in the desired position.

According to a preferred embodiment, a method for intubation of a patient comprises: providing an LMA and an endotracheal tube, wherein the endotracheal tube comprises a visualization device and wherein the endotracheal tube is adapted for passing through the LMA; positioning the LMA in the patient; guiding the endotracheal tube with the aid of the visualization device through the LMA for positioning in the trachea of the patient. The method preferably further comprises removing the LMA from the patient following the positioning of the endotracheal tube while leaving the endotracheal tube in position; connecting the visualization device to a display device prior to the guiding of the endotracheal tube through the LMA; connecting the LMA to a ventilator following the positioning of the LMA in the patient; disconnecting the LMA from the ventilator prior to the guiding of the endotracheal tube through the LMA; connecting the endotracheal tube to a ventilator following the positioning in the trachea of the patient; and disconnecting the ventilator and the visualization device from the endotracheal tube prior to the removing of the LMA.

The LMA preferably comprises an LMA cuff wherein the LMA cuff is inflated following the positioning of the LMA in the patient and wherein the LMA cuff is deflated prior to the removing of the LMA. The endotracheal tube preferably comprises a tracheal cuff wherein the tracheal cuff is inflated following the positioning in the trachea of the patient.

Preferably, the visualization device is housed interior and adjacent to the distal end of the endotracheal tube. The visualization device preferably comprises an image sensor selected from the group consisting of a CCD image sensor and a CMOS image sensor. The endotracheal tube preferably comprises a single ventilation lumen. The visualization device preferably comprises a lens at a distal end thereof, wherein the endotracheal tube comprises an injection connector in fluid communication with at least one nozzle wherein the at least one nozzle is positioned proximal to the lens and wherein the at least one nozzle is aimed to clean the lens. The endotracheal tube optionally comprises at least one murphy eye at the distal end thereof.

The visualization device preferably comprises a light source selected from the group consisting of: one or more LEDs, optical fiber, waveguide, light guide, and any combination of these. The endotracheal tube preferably comprises an external wall defining an external surface of the endotracheal tube; the wall comprising a plurality of channels formed within the wall, each channel having a proximal end adjacent to the endotracheal tube proximal end, the plurality of channels comprising an visualization channel having a distal end adjacent to the endotracheal tube distal end; a cleaning channel having a distal end adjacent to the endotracheal tube distal end, and a tracheal cuff channel having a distal end adjacent to the endotracheal tube distal end.

The endotracheal tube preferably comprises a visualization device cable and an visualization device connector, the cable having a proximal end connected to the visualization device connector and a distal end connected to the visualization device such that the image sensor connector is electrically connected to the visualization device and is in image transfer data communication with the image sensor, wherein the cable passes through the visualization channel.

According to another preferred embodiment, a system for intubation of a patient comprises: an LMA; an endotracheal tube, wherein the endotracheal tube comprises a visualization device and wherein the endotracheal tube is adapted for passing through the LMA; wherein the visualization device aids in guiding the insertion and positioning of the endotracheal tube in the patient via the LMA which has been previously positioned in the patient. The LMA is optionally removed from the patient following the positioning of the endotracheal tube while leaving the endotracheal tube in position. The visualization device is preferably connected to a display device prior to the guiding of the endotracheal tube through the LMA.

The LMA is optionally connected to a ventilator following the positioning of the LMA in the patient; wherein the LMA is disconnected from the ventilator prior to the guiding of the endotracheal tube through the LMA; and wherein the endotracheal tube is connected to a ventilator following the positioning in the trachea of the patient.

The ventilator and visualization device are preferably disconnected from the endotracheal tube prior to the removing of the LMA. The LMA preferably comprises an LMA cuff which is inflated following the positioning of the LMA in the patient and deflated prior to the removing of the LMA. The endotracheal tube preferably comprises a tracheal cuff and the tracheal cuff is inflated following the positioning in the trachea of the patient. The visualization device is preferably housed interior and adjacent to the distal end of the endotracheal tube. The visualization device preferably comprises an image sensor selected from the group consisting of a CCD image sensor and a CMOS image sensor. The endotracheal tube preferably comprises a single ventilation lumen. The visualization device preferably comprises a lens at a distal end thereof, and the endotracheal tube comprises an injection connector in fluid communication with at least one nozzle wherein the at least one nozzle is positioned proximal to the lens and wherein the at least one nozzle is aimed to clean the lens. The endotracheal tube optionally comprises at least one murphy eye at the distal end thereof. Optionally the visualization device comprises a light source selected from the group consisting of: one or more LEDs, optical fiber, waveguide, light guide, and any combination of these.

The endotracheal tube preferably comprises an external wall defining an external surface of the endotracheal tube; the wall comprising a plurality of channels formed within the wall, each channel having a proximal end adjacent to the endotracheal tube proximal end, the plurality of channels comprising an visualization channel having a distal end adjacent to the endotracheal tube distal end; a cleaning channel having a distal end adjacent to the endotracheal tube distal end, and a tracheal cuff channel having a distal end adjacent to the tracheal ventilation endotracheal tube distal end. The endotracheal tube preferably comprises a visualization device cable and an visualization device connector, the cable having a proximal end connected to the visualization device connector and a distal end connected to the visualization device such that the image sensor connector is electrically connected to the visualization device and is in image transfer data communication with the image sensor, wherein the cable passes through the visualization channel.

In one preferred embodiment a respiratory lumen is provided, preferably in the form of a single lumen, designed for oral or nasal insertion via the trachea and into a lung to maintain airway patency and/or deliver anesthetic, inhalation agent or other medical gases, and secure ventilation.

Most preferably the endotracheal tube may be made of medical grade materials for example including but not limited to plastic, rubber, polymers or silicone or the like materials as is known in the art.

Most preferably the endotracheal tube may provide for visualization during insertion and during continuous use of the oral cavity, esophagus, larynx trachea; the tracheal carina and at least a portion of a bronchus, optionally and more preferably portions of both bronchi.

Most preferably the integrated camera and light source provide continuous verification of the correct placement of the endotracheal tube. The continuous placement verification allows a caregiver the opportunity to detect any dangerous situation, for example cuff dislodgement, providing sufficient time to react to the situation as is necessary. Moreover blood and secretion accumulation or any other unexpected incidents during surgery, which might cause risk to the patient, may be observed.

In a preferred embodiment an endotracheal tube with an integrated image sensor is provided, for example including but not limited to CCD or CMOS camera, with a corresponding light source, for example including but not limited to a Light Emitting Diode ('LED') while optimizing the lumen patency for both adequate airflow performance through the tube. Most preferably the image sensor and corresponding light source are provided in a dedicated lumen along the length of the endotracheal tube. Most preferably the image sensor is further provided with at least one or more adjacent and integrated cleaning nozzle to ensure an open field of view.

Most preferably the integrated cleaning nozzle may be configured to be wholly embedded within the tube's wall in the form of a dedicated cleaning lumen running the length of the tube. Most preferably the length of the dedicated image sensor lumen is provided paralleled with the length of the tracheal lumen, therein both tracheal lumen and image sensor lumen are of essentially the same length. Optionally the length of the dedicated image sensor lumen may be provided according to the length of the bronchial lumen.

Optionally and preferably the tube of various embodiments utilizes a tracheal cuff. Optionally the tracheal cuff may be provided in varying shapes so as to better fit the trachea for example including but is not limited to spherical, elliptical, helical, hourglass, trapezoidal, or the like.

Within the context of this application the term "endotracheal tube" may be used interchangeably with any one of single lumen tube, single ventilation lumen tube, single lumen endotracheal tube, and single ventilation lumen endotracheal tube to collectively refer to a tube and/or catheter utilized for selectively ventilating a subject.

Optionally the image sensor may be a CCD image sensor or CMOS image sensor. Optionally, the first peripheral lumen further comprises a light source disposed proximal to the distal end and adjacent to the image sensor.

Optionally the light source may be selected from the group consisting of a LED, optical fiber, waveguide, light guide, and any combination thereof.

Most preferably the image sensor may be associated with an auxiliary device for example including but not limited to a display and power supply at the proximal end of the tube most preferably about the first lumen, through a single dedicated connector for example including but not limited to a USB connector, a mini or micro USB connector, or a LEMO connector.

Optionally the endotracheal tube may be adapted for non-invasive insertion through the oral cavity or nasal cavity. Optionally the endotracheal tube may be adapted for insertion through an external port or incision. Optionally the endotracheal tube may be adapted for insertion through a surgical procedure or other invasive procedure.

Unless otherwise defined, all technical and scientific terms used herein have the same meaning as commonly understood by one of ordinary skill in the art. The materials, methods, and examples provided herein are illustrative only and not intended to be limiting. The terms tube, lumen and channel may be used interchangeable herein. The terms visualization device, image sensor, and camera are used interchangeably herein.

BRIEF DESCRIPTION OF THE DRAWINGS

The embodiments herein are described, by way of example only, with reference to the accompanying drawings. With specific reference now to the drawings in detail, it is stressed that the particulars shown are by way of example and for purposes of illustrative discussion of the preferred embodiments of the present disclosure only, and are presented in order to provide what is believed to be the most useful and readily understood description of the principles and conceptual aspects of the embodiments. In this regard, no attempt is made to show structural details of the embodiments in more detail than is necessary for a fundamental understanding of the exemplified embodiments. The description taken with the drawings making apparent to those skilled in the art how the several forms of the disclosed embodiments may be embodied in practice. In the drawings.

DESCRIPTION OF EMBODIMENTS OF THE INVENTION

The principles and operation of the disclosed embodiments may be better understood with reference to the drawings and the accompanying description. The following reference labels are used throughout the drawings to refer to objects having similar function, meaning, role, or objective:

Endotracheal intubation system 100
Endotracheal tube 101
Visualization device 102
Tip 103
Tracheal cuff 104
Inner tube diameter 105
Outer tube diameter 106
Nozzles 107
Visualization cable 109
Ventilation lumen 110
Inflation tube 111
Inflation connector 112
Injection tube 113
Murphy eyes 114
Proximal end 115
Distal end 116
Aperture 117
Injection port 118

Visualization connector 119
Ventilator connector 120
Lens 121
Visualization channel 122
Tracheal cuff inflator port 123
Tracheal cuff inflator channel 124
Light source 126
Pilot balloon 128
Tube wall 130
Seal 132
Injection channels 133
Display device 140
Visualization notch 142
Inflation notch 144
Injection notch 146
Stylet 160
LMA 200
LMA tube 201
LMA tracheal opening 202
LMA outer opening 203
LMA cuff 204
LMA connector 208
LMA inflation tube 211
LMA inflation connector 212
Proximal end 215 of LMA 200
Distal end 216 of LMA 200
LMA pilot balloon 228
LMA system 300

In some embodiments an endotracheal tube with visualization capabilities that also features a laryngeal mask is disclosed. The endotracheal tube preferably has continuous and long term visualization capabilities, such that at least a portion of the patient's airways can be visualized for an extended period of time. By "extended period of time" it is meant at least one hour, two hours and so forth up to twenty-four hours; at least one day, two days, and so forth up to one week; one week, two weeks and so forth up to one month; or any period of time in between measured in at least increments of one minute. The endotracheal tube preferably features a single ventilation lumen.

The portion of the patient's airways that can be visualized preferably includes (upon entry) the oral cavity, esophagus, larynx and trachea; and (after being placed at the location for the extended period of time) the tracheal carina and at least a portion of a bronchus, optionally and more preferably portions of both bronchi.

Figure 1:
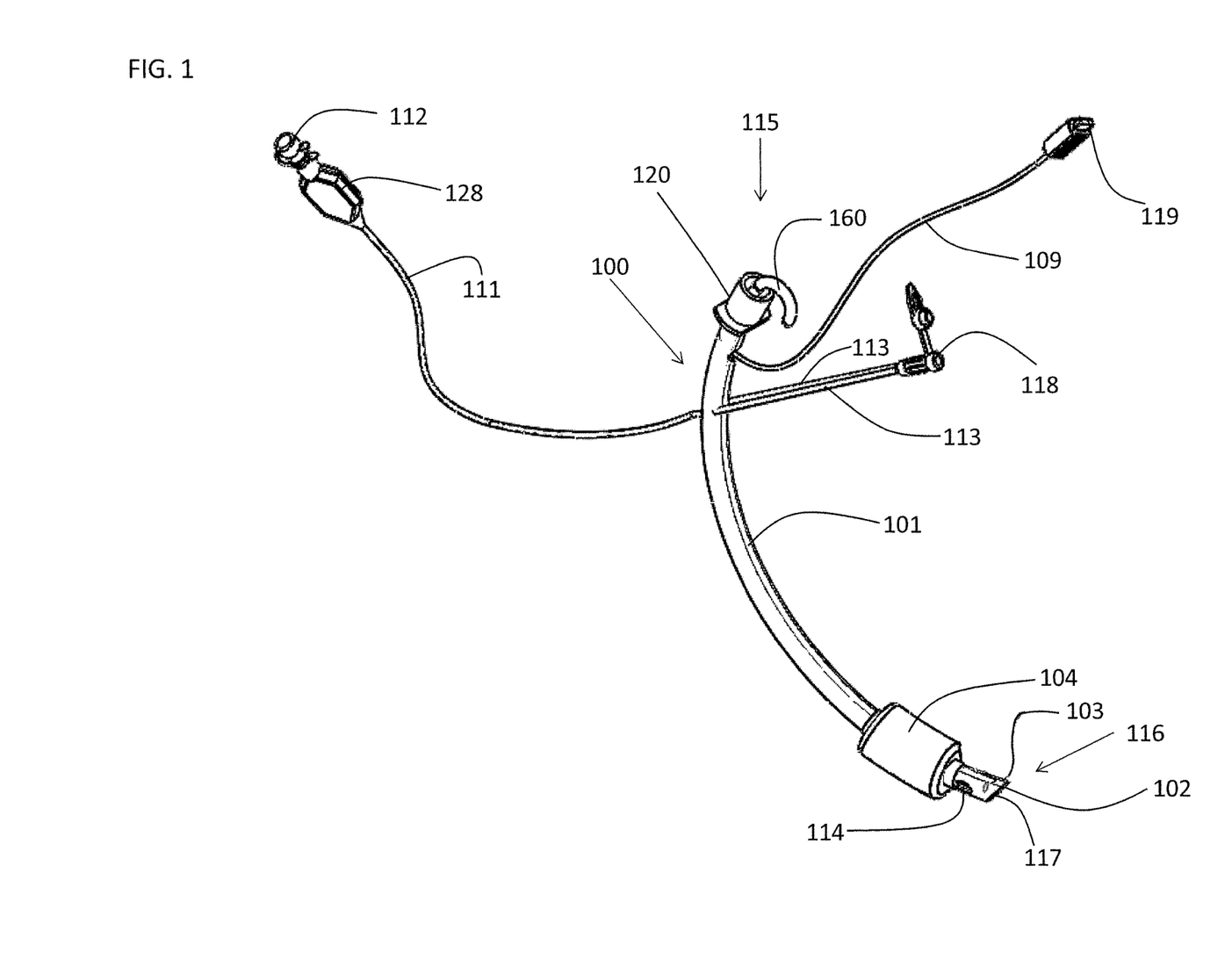
FIG. 1 shows an isometric view of an embodiment of an endotracheal tube.
Figure 2:
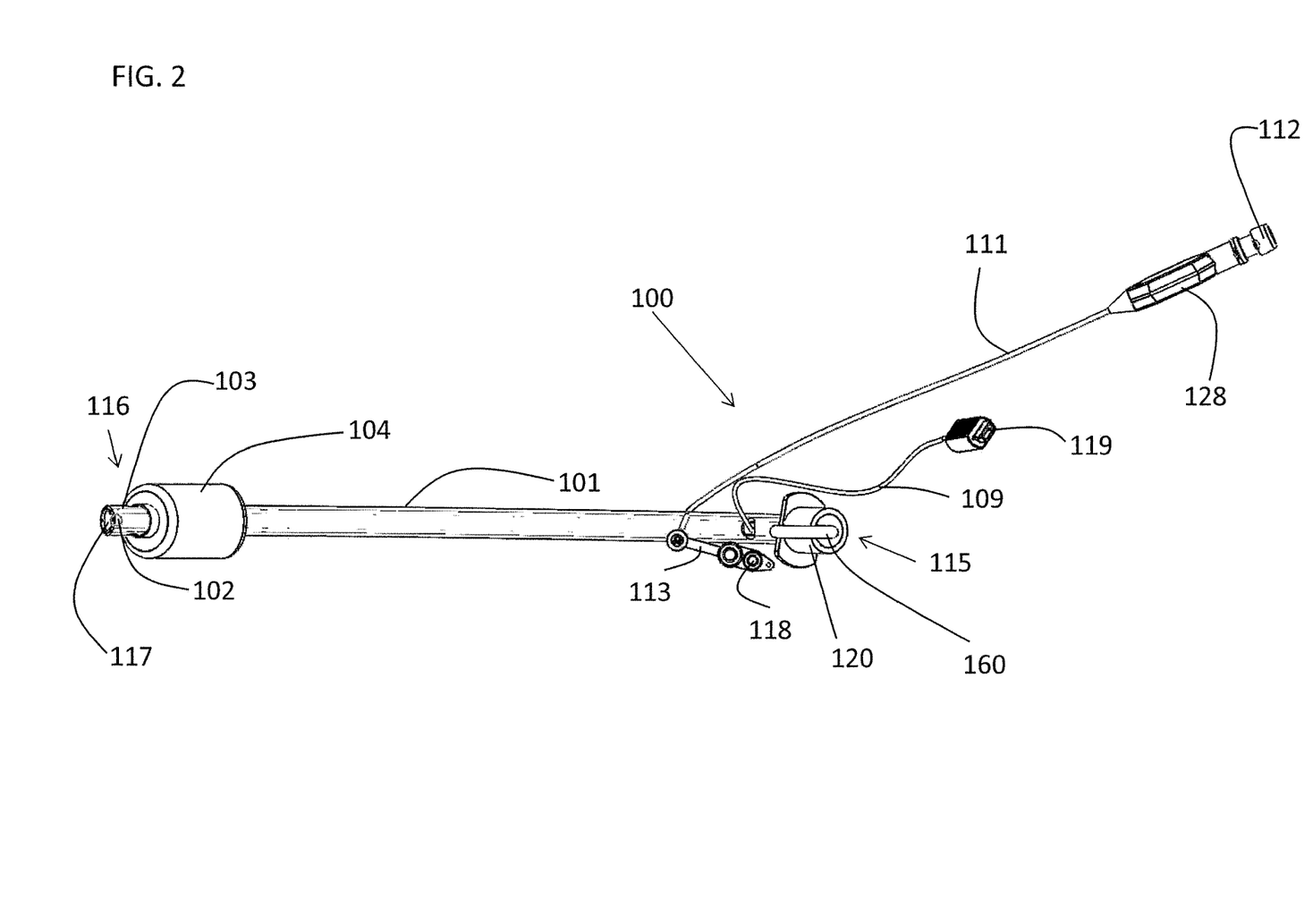
FIG. 2 shows another view of the embodiment of the endotracheal tube of FIG. 1.

FIGS. 1 and 2 show isometric and side views of an embodiment of an endotracheal intubation system 100 including an endotracheal tube 101 for insertion into a subject (not shown). Endotracheal tube 101 includes a proximal end 115 opposite a distal end 116. As described herein, the terms "proximal" and "distal" are defined with regard to the point of entry to the subject, so that proximal end 115 as shown remains outside the subject, while distal end 116 as shown enters the subject. Endotracheal intubation system 100 optionally also includes a stylet 160.

A ventilator connector 120 connects endotracheal tube 101 to a breathing circuit coupled to a ventilator (not shown). A tip 103 of endotracheal tube 101 is located at distal end 116. Tip 103 features an aperture 117 for permitting two-way passage of fluids, including but not limited to gasses, into and out of the subject (not shown). The diameter of aperture 117 is defined with regard to an inner diameter of tube 101 as described in greater detail below.

Endotracheal tube 101 includes a visualization device 102 located at tip 103 for visualizing at least a portion of the airways of the subject as described above. Visualization device 102 may optionally comprise any suitable type of image sensor, including but not limited to a CCD image sensor or CMOS image sensor. Visualization device 102 is optionally in data communication with a visualization connector 119 through a visualization cable 109 (shown in FIG. 3B) to permit image data obtained with a visualization device 102 to be transferred to a display device 140 (shown in FIG. 3E), such as a video monitor. By "data communication" it is meant any type of communication means for transmitting data, including but not limited to wired or wireless (not shown) communication. If visualization connector 119 is not present, optionally visualization device 102 may communicate directly, wirelessly with an external device (not shown). As shown, in a wired connection embodiment, connector 119 is connected to visualization device 102 via visualization cable 109 which passes through the wall 130 (FIG. 3D) of tube 101 as described further below. Visualization cable 109 also provides electrical power to visualization device 102.

Endotracheal tube 101 also includes a tracheal cuff 104 located between proximal end 115 and distal end 116, but preferably closer to distal end 116. Tracheal cuff 104 is preferably deflated upon insertion of endotracheal tube 101 to the subject and is then inflated once endotracheal tube 101 is in place to maintain the position of endotracheal tube 101 within the subject. Cuff 104 is here shown as inflated. Inflation is controlled through a tracheal cuff connector 112, connected to an inflation tube 111 which is in fluid communication with cuff 104. Connector 112 comprises a pilot balloon 128 which provides an indication of the inflation status of cuff 104. When balloon 128 is inflated, cuff 104 is also inflated.

Endotracheal tube 101 further includes an injection port 118 connected to injection tubes 113. Optionally and preferably, injection tubes 113 are provided, for example, to permit injection of fluids for cleaning visualization device 102. Injection tubes 113 are in fluid communication with nozzles 107 (described further below with reference to FIG. 3A) positioned adjacent visualization device 102. Optionally only one injection tube is provided.

Optionally and preferably, endotracheal tube 101 features at least one and preferably a plurality of Murphy eyes 114 to provide adequate airflow performance through the tube since aperture 117 is narrowed due to the presence of visualization device 102. Murphy eyes 114 also permit entry of air to the subject in case aperture 117 becomes blocked. Optional stylet 160 is inserted into endotracheal tube 101 and is used to shape endotracheal tube 101 prior to insertion or during insertion of tube 101 into a patient as known in the art. Stylet 160 is then removed.

Figure 3A:
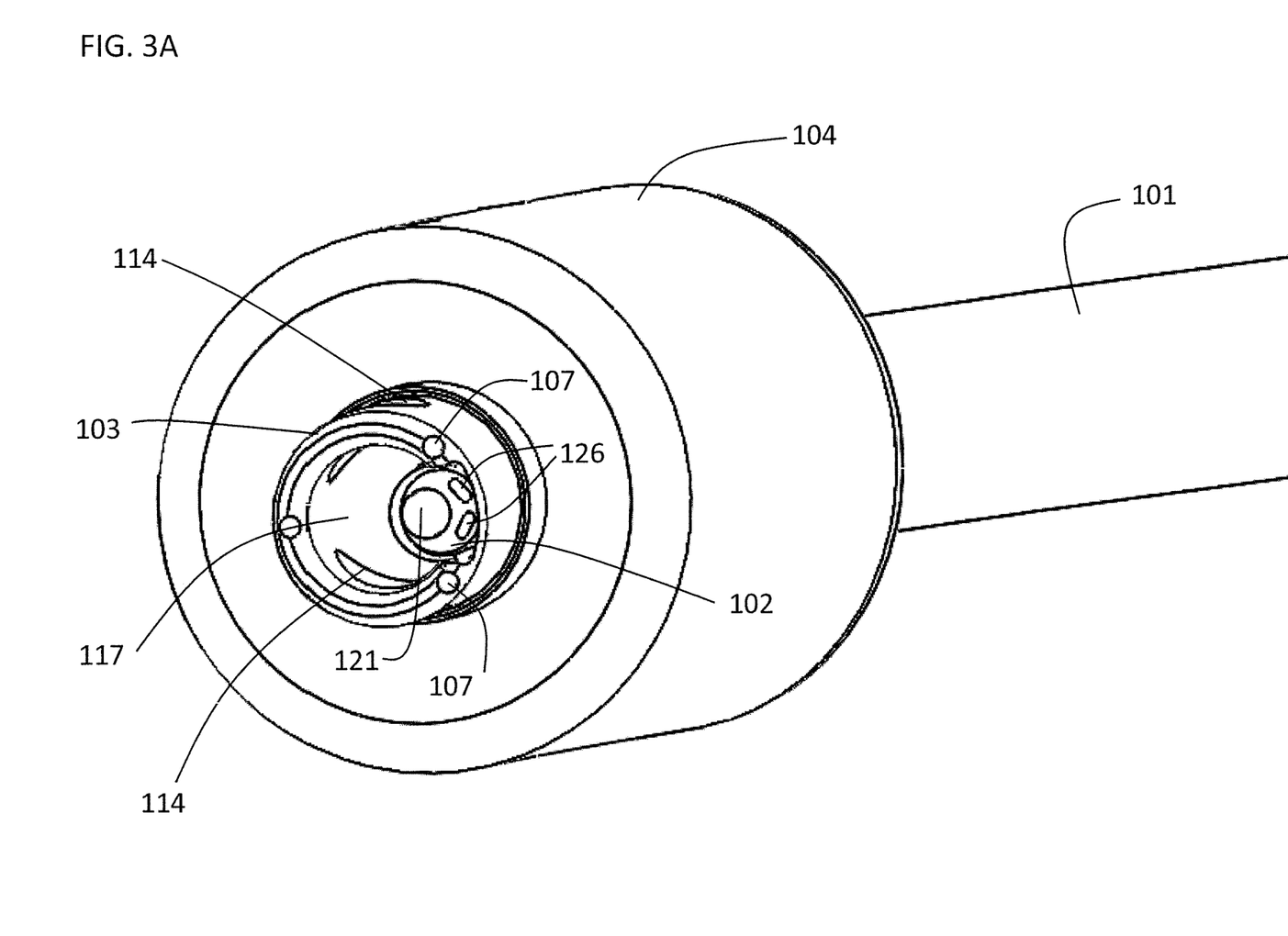
FIG. 3A shows an enlarged view of the distal end of the endotracheal tube of FIG. 1.

Reference is now made to FIG. 3A which shows an enlarged view of tip 103 of endotracheal tube 101. FIG. 3A shows visualization device 102, including a lens 121, a pair of light sources 126 adjacent lens 121, and a pair of nozzles 107 located on each side of visualization device 102. Visualization device 102 is provided for visualization of the subject as tip 103 is inserted into the subject. After insertion, visualization device 102 is used to confirm that endotracheal tube 101 remains correctly positioned within the subject by visualizing the field (area) surrounding tip 103. Lens 121 covering lenses and an image sensor (not shown). Light source 126 may comprise one or more LEDs, optical fibers, a waveguide, a light guide, or any combination of these. Visualization device 102 preferably has a horizontal angle of view of between 50°-120°, more preferably between 70° and 80° and more preferably 76°. Visualization device 102 preferably has a vertical angle of view of between 50°-120°, more preferably between 50° and 60° and more preferably 56°. The visualization device preferably has a diagonal angle of view of between 50°-120°, more preferably between 90° and 110° and more preferably 100°. The visualization device preferably has a focus range of between 5-150 mm and more preferably between 12-60 mm.

Nozzles 107 are positioned and angled to aim a stream of fluid, such as a liquid or gas, toward or at visualization device 102 in order to clean lens 121. In one example, visualization device 102 and light sources 126 are positioned in a housing embedded in a channel formed in the wall 130 (shown in FIG. 3D) of endotracheal tube 101. In one example, nozzles 107 comprise the distal ends of fluid injection channels formed in the wall of endotracheal tube 101. In one variation, nozzles 107 are made by forming apertures at an angle to a longitudinal axis of the fluid injection channels and fluidly coupling therewith. The apertures may be made by laser drilling the apertures on the wall of the endotracheal tube 101. The angle at which the nozzles are formed enables aiming of the fluid toward visualization device 102. In another example, nozzle inserts are inserted into the fluid injection channels. A nozzle insert may comprise an aperture formed at an angle to the longitudinal axis of a corresponding fluid injection channel and may be rotated to aim the fluid toward visualization device 102.

Figure 3B:
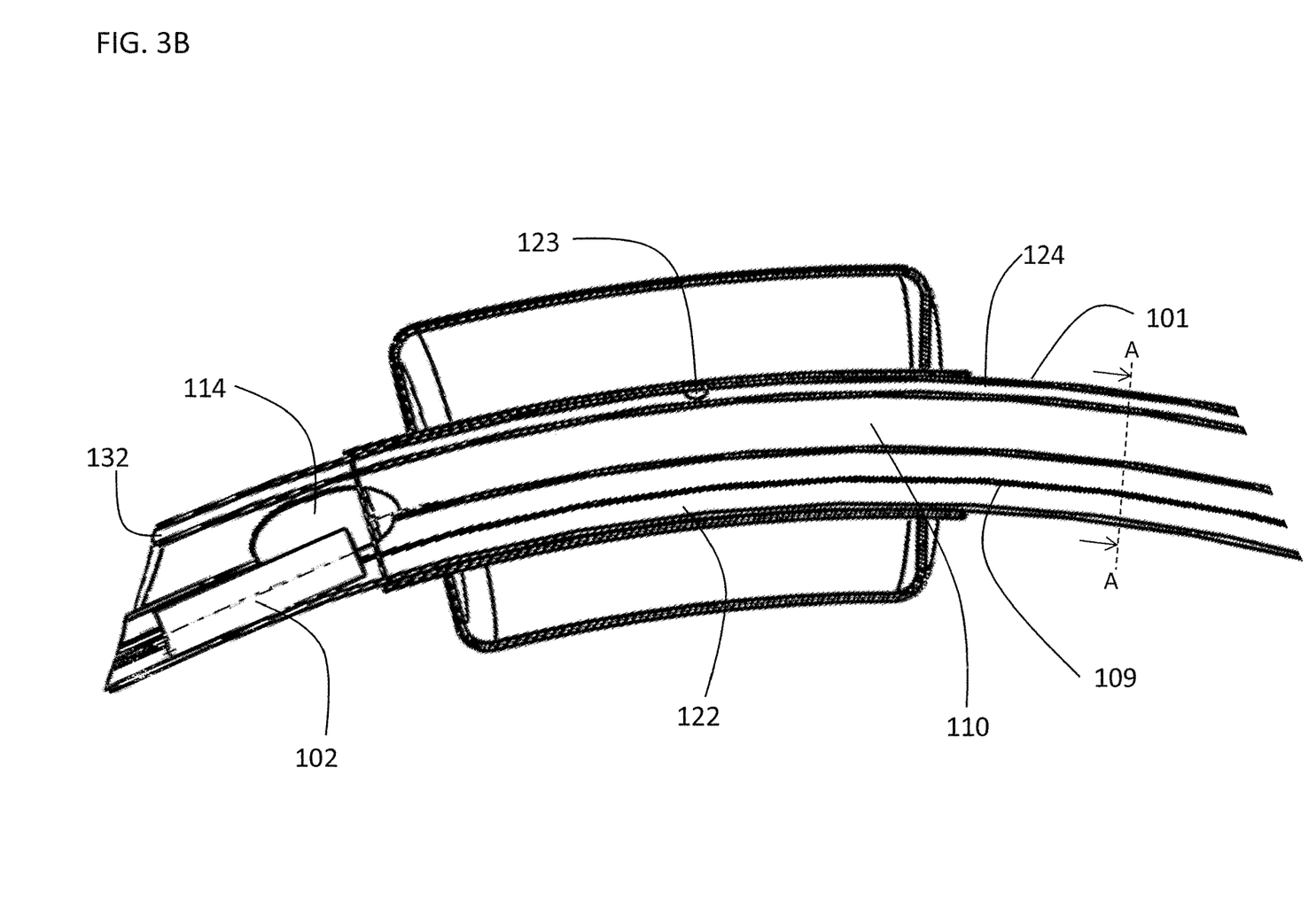
FIG. 3B shows a cutaway view of the distal end and inflatable cuff of the endotracheal tube of FIG. 1.
Figure 3C:
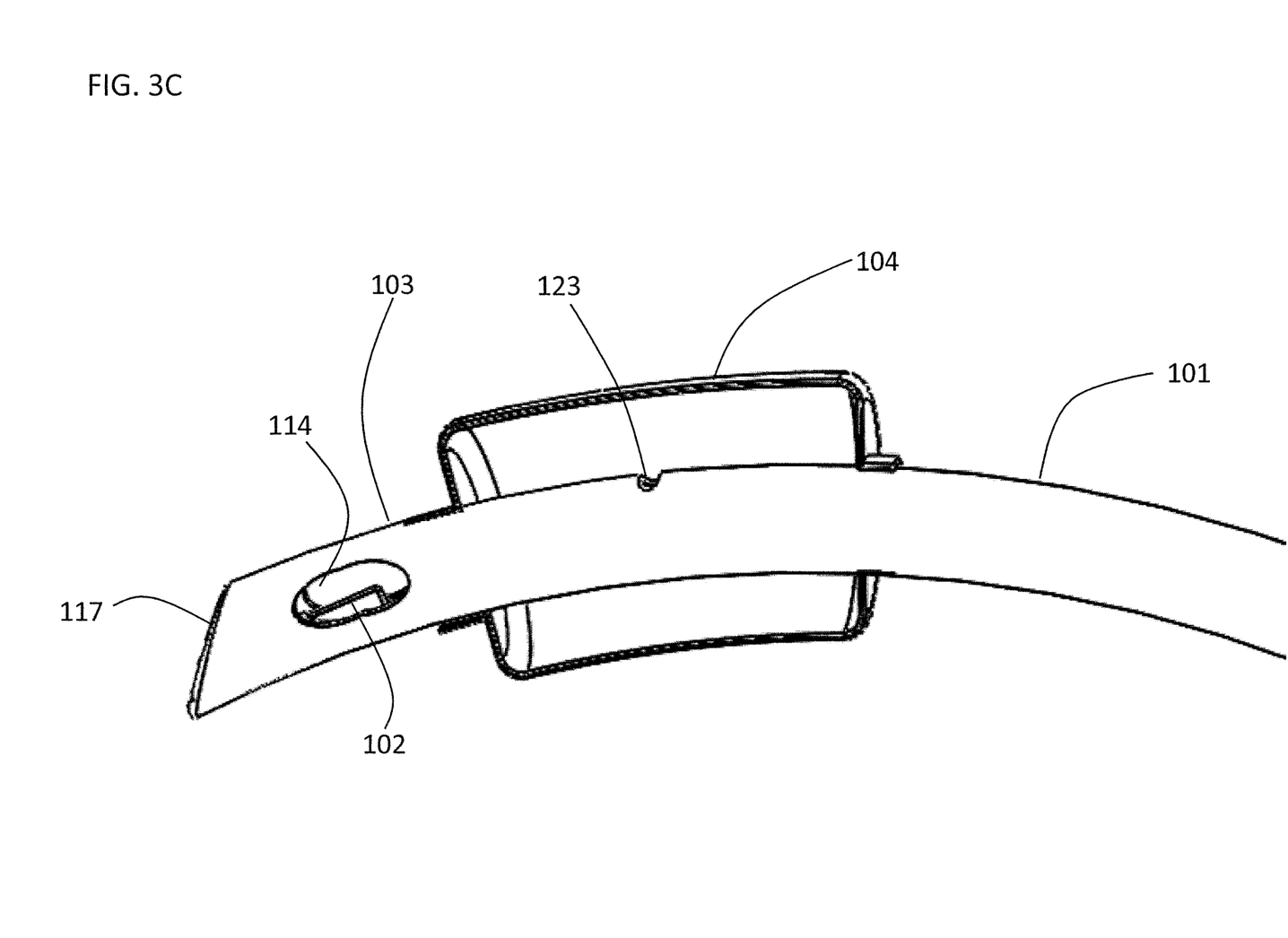
FIG. 3C shows a partial cutaway view of the endotracheal tube of FIG. 1.

Reference is now made to FIGS. 3B and 3C which show complete and partial cut-away views of the illustrative single lumen endotracheal tube 101 and tracheal cuff 104. As shown, endotracheal tube 101 comprises an external wall 130 with a plurality of internal channels or lumens including a ventilation lumen 110, a visualization channel 122, and an inflation channel 124. Ventilation lumen 110 is provided for conveying gasses into and out of the subject; as such, ventilation lumen 110 is typically the largest lumen within endotracheal tube 101. Ventilation lumen has a proximal end adjacent connector 120 and a distal end at aperture 117.

Visualization channel 122 is embedded in wall 130 of endotracheal tube 101 and preferably provides a path for cable 109 for connecting visualization device 102 to visualization connector 119. Visualization channel 122 has a proximal end adjacent to ventilator connector 120 and a distal end that houses visualization device 102.

Tracheal cuff 104 is fixedly attached to the external surface of endotracheal tube 101. Tracheal cuff 104 is inflated through a tracheal cuff inflator port 123 which extends from ventilation channel 124 and opens into the inner volume of cuff 104 as shown. Tracheal cuff inflator port 123 receives air from enclosed tracheal cuff inflator channel 124, which is embedded in the wall 130 of endotracheal tube 101 and which is in fluid communication at its proximal end with inflation tube 111, which in turn receives air through inflation connector 112 as previously described. Tracheal cuff inflator channel 124 is sealed at its distal end by a seal 132. Air may be injected into inflation connector 112 via an injection means such as a syringe or may be via mechanical means. A plurality of Murphy eyes 114 are provided as shown.

Figure 3D:
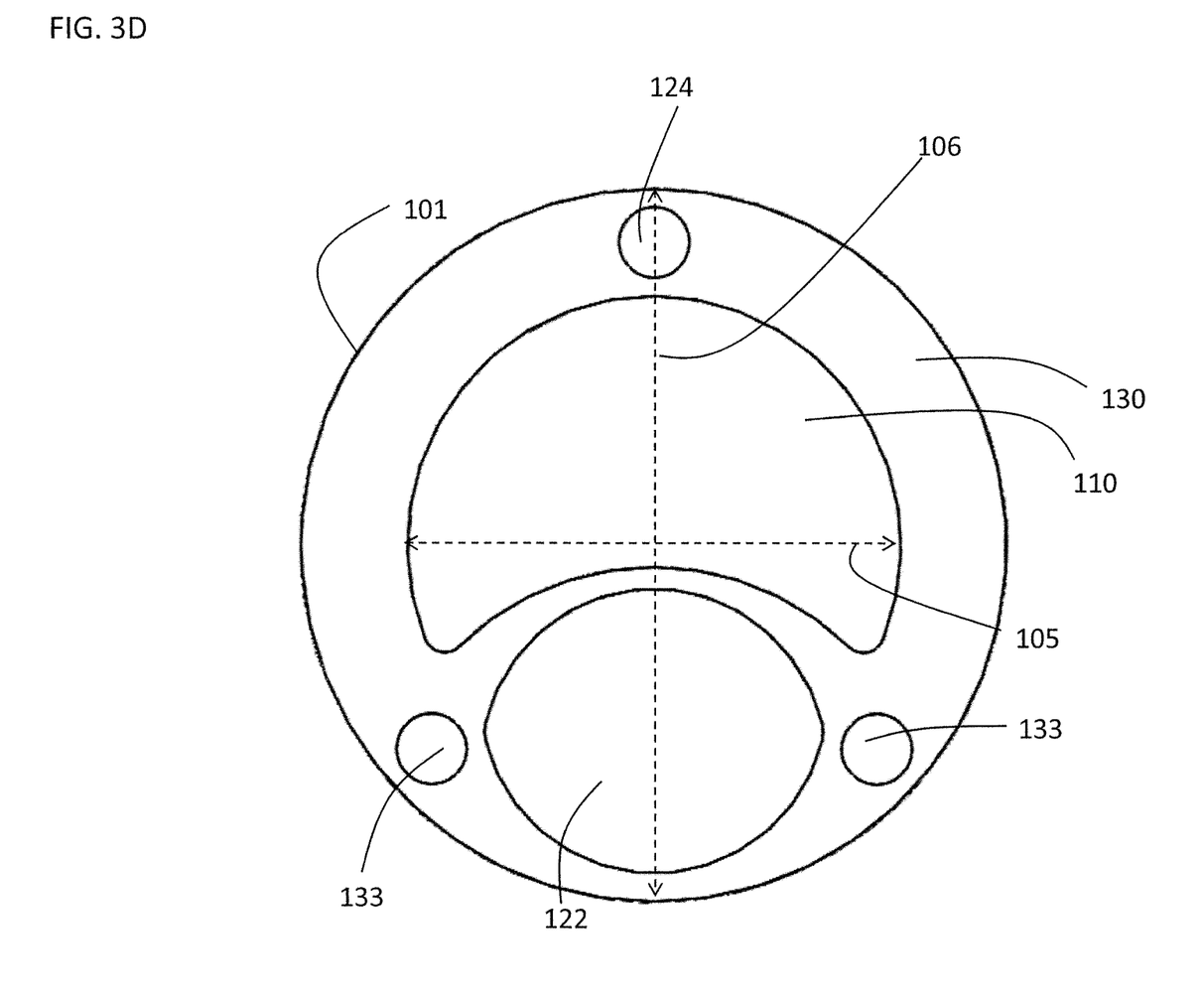
FIG. 3D shows a cross-section of the tube portion of the endotracheal tube of FIG. 1 illustrating various lumens and channels.

Reference is now made to FIG. 3D which shows a cross-section A-A as shown in FIG. 3B of an endotracheal tube according to some embodiments. FIG. 3D shows channels embedded in the external wall 130 of endotracheal tube 101, including ventilation lumen 110, visualization channel 122, tracheal cuff inflator channel 124, and a pair of fluid injection channels 133 that feed nozzles 107. Injection channels 133 are enclosed channels and are in fluid communication with injection tubes 113. The inner space within endotracheal tube 101 defines ventilation lumen 110.

More preferably, the outer diameter 106 of the endotracheal tube is in a range of from 10 mm to 11 mm, such that the maximum outer diameter 106 of the endotracheal tube along the its length extending from the proximal end until tip 103 is preferably no more than 11 mm. At the tip 103 of endotracheal tube 101 the diameter is larger to accommodate the visualization device 102 and the maximum diameter of tip 103 preferably does not exceed 13 mm. Optionally, in some embodiments, the outer diameter of endotracheal tube 101 may not exceed 14 mm at any point along its length. In some embodiments, the inner diameter 105 may range from 7 mm to 8 mm.

Figure 3E:
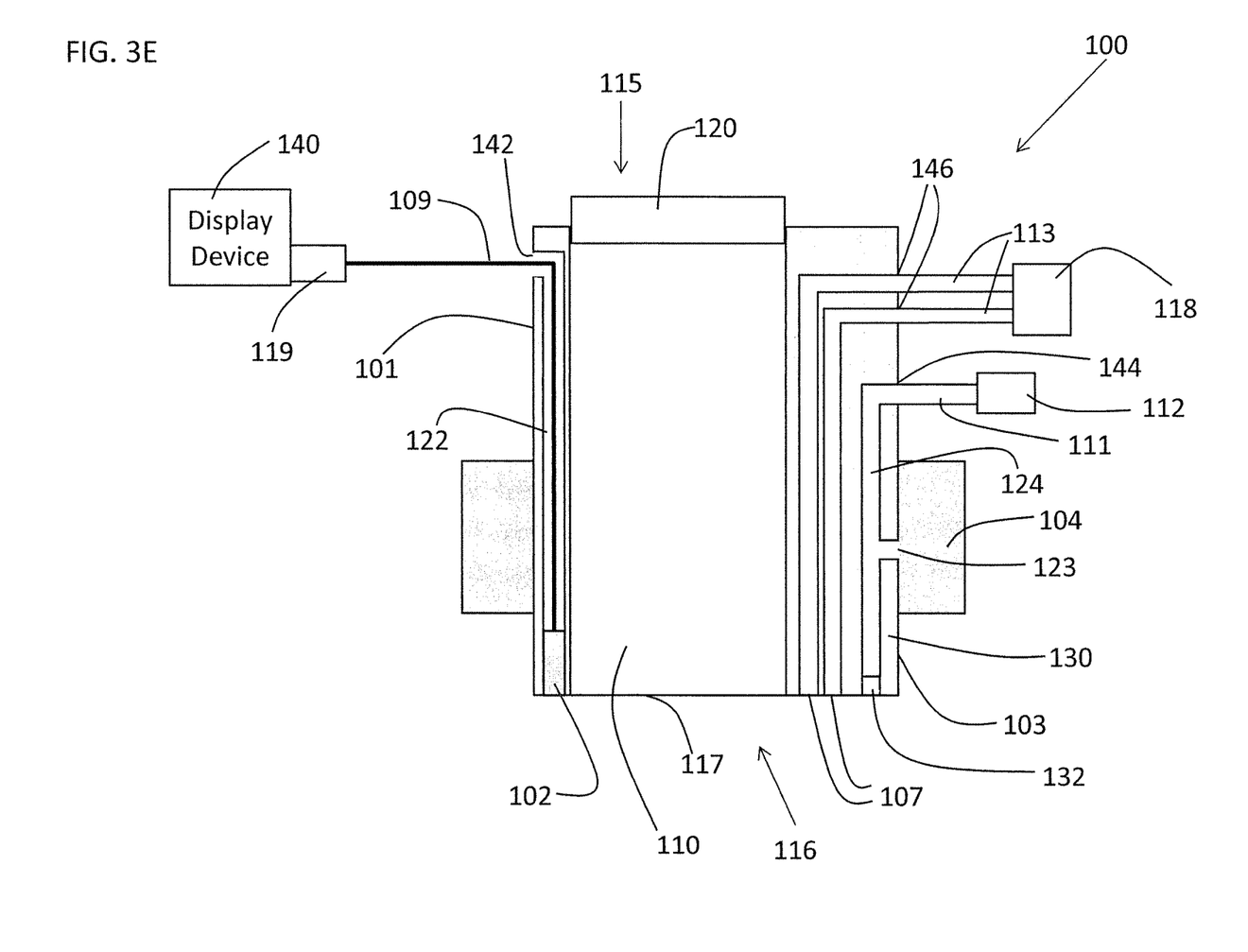
FIG. 3E is a schematic diagram showing the end-to-end tubes, channels and lumens provided within an endotracheal tube according to some embodiments.

Reference is now made to FIG. 3E which is a schematic diagram showing the end-to-end tubes, channels and lumens provided within an endotracheal tube according to some embodiments. As shown, endotracheal tube 101 comprises wall 130 with embedded channels including inflator channel 124 for inflating tracheal cuff 104. Inflator channel 124 is in fluid communication at its proximal end with tube 111 which is connected to connector 112. Inflation tube 111 enters the proximal end of endotracheal tube 101 into wall 130 at inflation notch 144 and is connected thereafter to inflation channel 124. Inflation channel 124 is sealed at its distal end by seal 132 and is in fluid communication with the interior of cuff 104 via inflator port 123.

Enclosed injection channels 133 are in fluid communication at their distal ends with nozzles 107 and at their proximal ends with injection tubes 113 which in turn are connected to injection port 118. Injection tubes 113 enter the proximal end of endotracheal tube 101 into wall 130 at injection notches 146 and are connected thereafter to injection channels 133.

Visualization channel 122 provides a path through wall 130 for visualization cable 109 and additionally houses visualization device 102 interior and adjacent to the distal end of visualization channel 122. Cable 109 is connected at its proximal end to connector 119 which is optionally connected to optional display device 140 for displaying still images or video received from visualization device 102. Cable 109 enters channel 122 via visualization notch 142.

The inner space within endotracheal tube 101 defines ventilation lumen 110 which is provided at its proximal end with connector 120 and at its distal end with aperture 117 and Murphy eyes 114.

Figure 4:
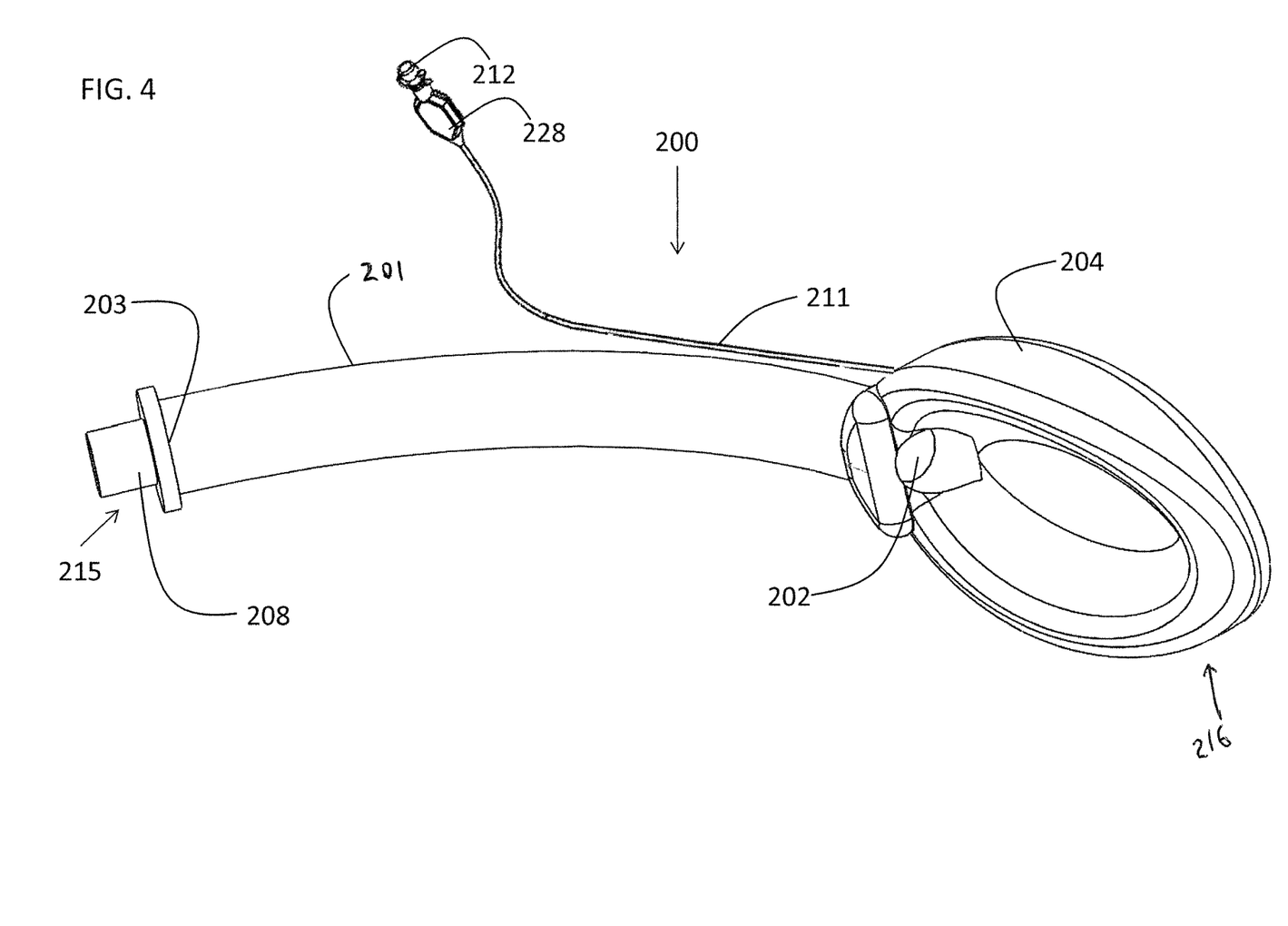
FIG. 4 shows an embodiment of an LMA.

FIG. 4 shows an embodiment of an LMA 200 featuring an LMA tube 201 for bi-directional transmission of fluids, which optionally and preferably include gases. LMA tube 201 comprises an LMA outer opening 203 at a proximal end 215 of LMA 200. Removable LMA connector 208 is shown inserted into opening 203. An LMA tracheal opening 202 is located at a distal end of tube 201, near or at inflatable LMA cuff 204 which is located at a distal end 216 of LMA 200. LMA cuff 204 is connected to LMA inflation tube 211 which in turn is connected to LMA inflation connector 212. Connector 212 further comprises an LMA pilot balloon 228 providing an indication of the inflation status of LMA cuff 204. LMA cuff 204 is inflated by pumping air into inflation connector 212. Outer opening 203 and tracheal opening 202 are in fluid communication via tube 201. LMA 200 preferably has an internal diameter of between 12 and 13 mm.

Figure 5A:
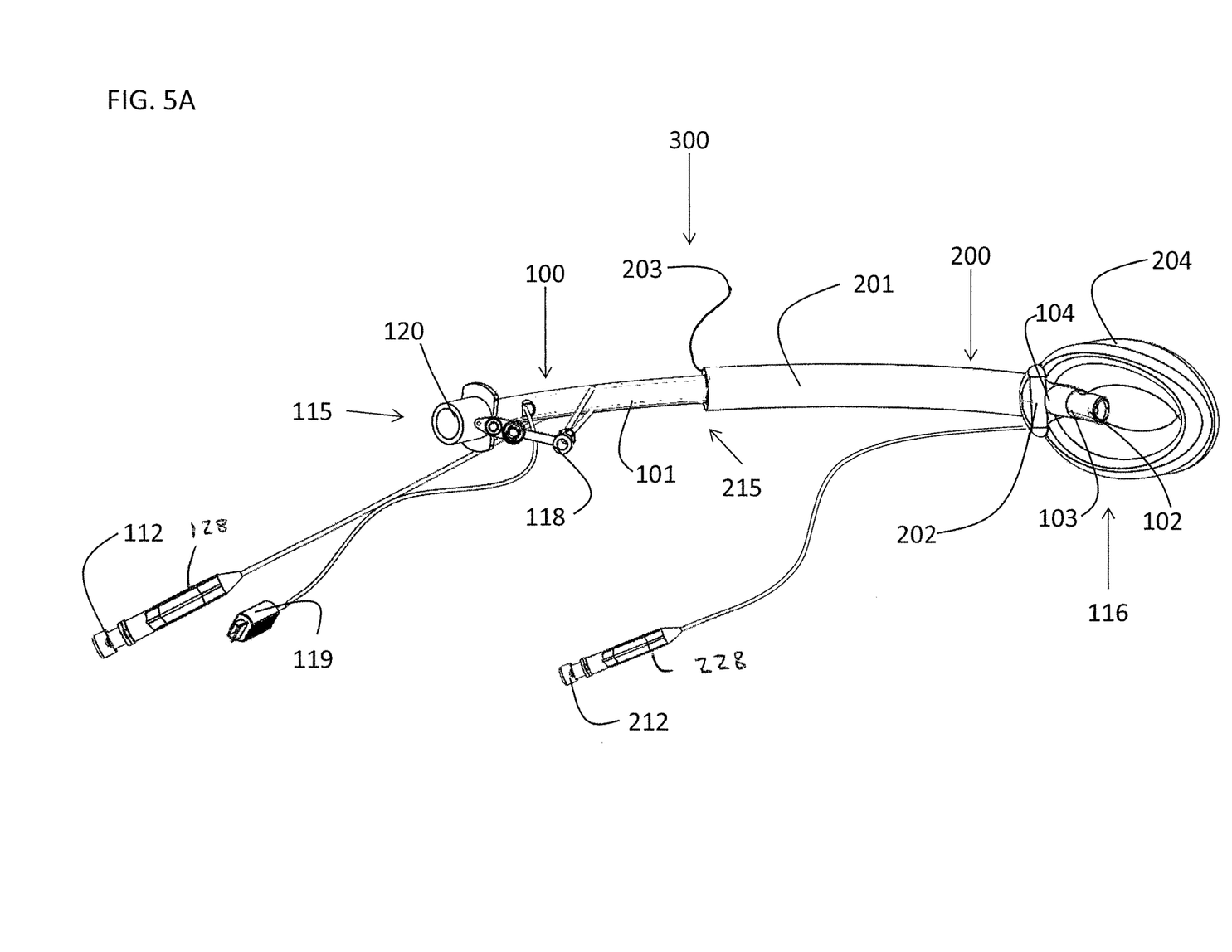
FIGS. 5A and 5B show perspective and side views of an endotracheal tube placed within an LMA to form an LMA system 300 according to some embodiments.

FIG. 5A shows endotracheal tube 101 placed within LMA 200 to form an LMA system 300 according to some embodiments. To enable insertion of endotracheal tube 101 into LMA 200, LMA connector 208 (not shown in FIG. 5A) is removed, and cuff 104 is deflated. Use of LMA 200 eases the insertion and positioning of endotracheal tube 101 as LMA 200 provides a guide for endotracheal tube 101 to ease the positioning thereof in the trachea (not shown). Once endotracheal tube 101 is positioned, tracheal cuff 104 is inflated to secure endotracheal tube 101 before LMA 200 is removed from the patient leaving endotracheal tube 101 in position. The external diameter of tube system 100 is such that it can pass completely through the inner diameter of tube 201 of LMA 200 in either direction. Thus LMA 200 can be removed from the patient over endotracheal tube 101 while endotracheal tube 101 is in position. Additionally the positions of notches 142, 144, and 146 are staggered and are not equidistant from the proximal end of endotracheal tube 101 to allow for each of tubes 111 and 113 as well as cable 109 to pass through LMA 200. Further, visualization connector 119 is sized to pass through the inner diameter of LMA tube 201. Connector 120 may be placed on endotracheal tube 101 after LMA 200 has been removed.

Figure 5B:
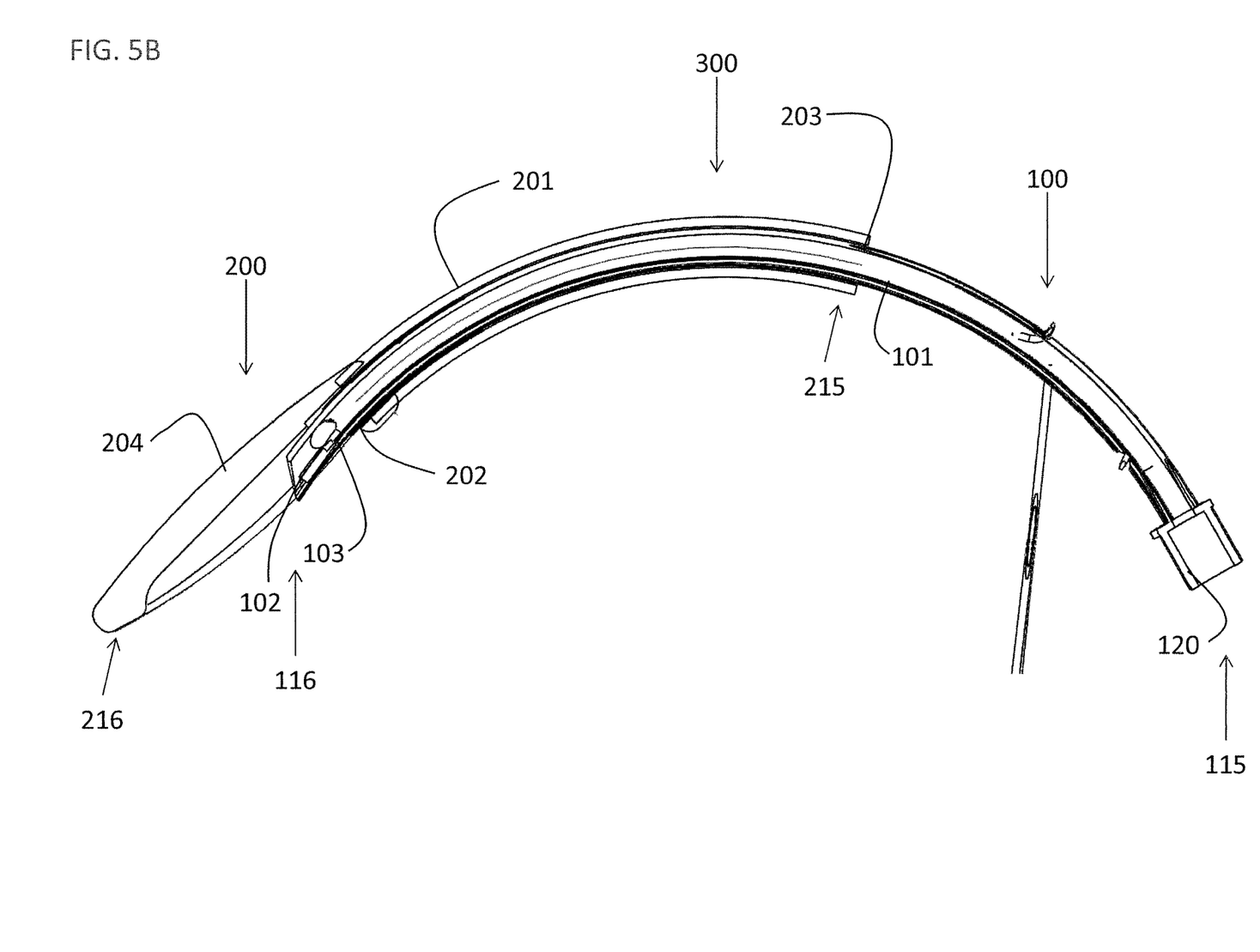

FIG. 5B shows a cut-away view of LMA system 300. Proximal end 216 and distal end 215 of LMA 200 are shown with LMA 200 placed over endotracheal tube 101, such that LMA tube 201 slides over endotracheal tube 101. Proximal end 115 and distal end 116 of endotracheal tube 101 are visible. LMA tracheal opening 202 and a LMA outer opening 203 permit gasses to flow into and out of the patient (not shown) via the inserted tube system 100.

Figure 5C:
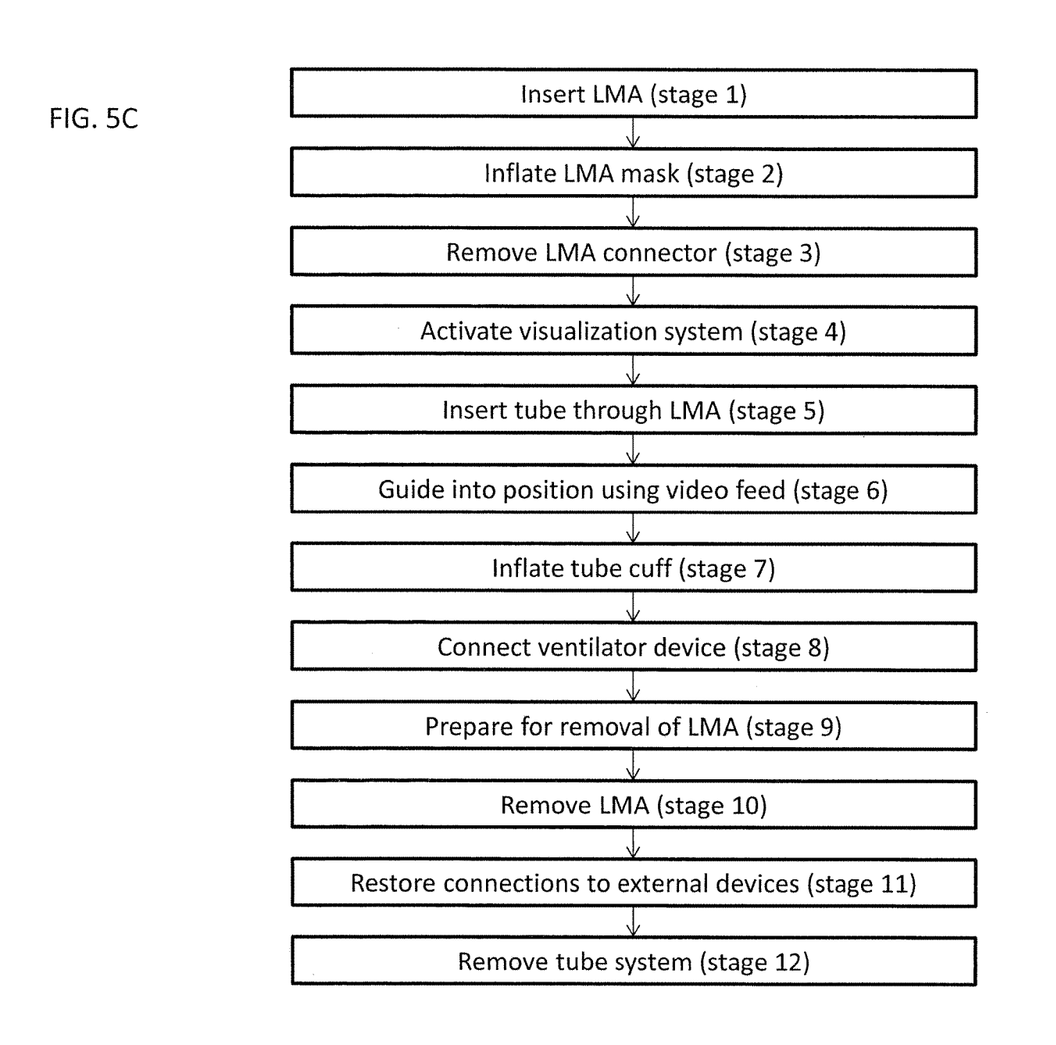
FIG. 5C is a flow diagram describing a preferred method for intubation of a patient using the LMA system of FIGS. 5A and 5B.

Reference is now made to FIG. 5C which is a flow diagram describing a preferred method for intubation of a patient using the LMA system described herein according to some embodiments. In the described method of FIG. 5C, the LMA 200 is first positioned in the patient before the tube system 100 is inserted. At this stage the LMA cuff 204 of LMA 200 is deflated. In stage 1, a lubricant is applied to the external surface of the LMA to ease insertion and the LMA 200 is inserted into the patient via the patient's mouth and positioned over the trachea of the patient.

In stage 2, LMA cuff 204 is inflated to secure LMA 200 in position. At this stage the LMA may be connected to a ventilation device if required. In stage 3 connector 208 is removed along with any ventilation device connection if in place. In stage 4 visualization connector 119 is connected to display device 140 and visualization device 102 of tube system 100 is activated. The display device provides power to the visualization device and displays the image and/or video captured by the visualization device. In stage 5, a lubricant is applied to the external surface of endotracheal tube 101 to ease its insertion through LMA tube 201 and tube system 100 is inserted into the patient via the in-place LMA 200. Optionally stage 4 (connection of the visualization device) may take place after stage 5 or at any time prior to insertion of endotracheal tube 101 into the subject. In stage 6, with the aid of the video feed from device 102 tube system 100 is passed into the trachea of the patient until it is in the correct position.

With the tube system 100 in place, cuff 104 is now inflated at stage 7. In stage 8 a ventilation device may be connected to ventilator connector 120. Optionally, stage 8 (ventilation) may take place before stage 7 (cuff inflation). Optionally, a fluid is injected through injection port 118 that will exit through nozzles 107 to clean lens 121.

Once cuff 104 is inflated, tube system 100 is secured in position and in stages 9 to 11 LMA 200 is removed. In stage 9 preparation is made for removal of LMA 200. Stage 9 includes deflation of LMA cuff 204, removal of any connection of a ventilation device from ventilator connector 120, and disconnection of connectors 119 (visualization), injection port 118, and 113 (cuff inflation) from external systems or devices. Then in stage 10, LMA 200 is removed by sliding it off tube system 100. In stage 11, connection is restored to a ventilation device through ventilator connector 120, and connectors 119 (visualization), injection port 118 and 113 (cuff inflation) are reconnected to external systems.

In stage 12, when endotracheal tube 101 is no longer required, cuff 104 is deflated and endotracheal tube 101 is removed from the patient. Optionally, LMA 200 is left in position with endotracheal tube 101 and stages 9 and 10 are performed along with stage 12 or both LMA 200 and endotracheal tube 101 are removed together.

Optionally, tube system 100 is inserted into LMA 200 before insertion of LMA system 300 into the patient. In this optional method, visualization device of tube 100 can be used to guide LMA 200 into position in the patient. Once tube system 100 is secured by cuff 104, LMA 200 may optionally be removed from the patient.

While various embodiments been described with respect to a limited number of embodiments, it will be appreciated that many variations, modifications and other applications of the disclosure may be made.

What is claimed is:

1. A method for intubation of a patient comprising:
   positioning a laryngeal mask airway (LMA) in the patient, the LMA comprising a tube connected at a distal end thereof to a mask portion;
   positioning an endotracheal tube in the LMA, the endotracheal tube sized and configured to pass through the tube of the LMA and comprising a visualization device at a distal end of the endotracheal tube, the visualization device structured to provide visual images of a distal space distal of the visualization device;
   guiding the endotracheal tube through the LMA while visualizing the distal space;
   prior to said guiding of said endotracheal tube through said LMA, connecting said visualization device to a display device; and
   positioning the distal end of the endotracheal tube in the trachea of the patient; and
   removing said LMA from the patient following said positioning while leaving said endotracheal tube positioned in the trachea.

2. The method of claim 1, wherein said endotracheal tube comprises a single ventilation lumen, a fluid injection channel formed in a wall of the endotracheal tube and extending longitudinally adjacent the single ventilation lumen, and a nozzle fluidly coupled to the fluid injection channel, and wherein said visualization device comprises a lens at a distal end thereof, wherein said endotracheal tube further comprises an injection connector in fluid communication with said nozzle, the method further comprising:
   injecting a fluid through the injection connector to discharge the fluid through the nozzle to clean said lens.

3. The method of claim 1, further comprising:
   connecting said LMA to a ventilator following said positioning of said LMA in the patient;
   disconnecting said LMA from said ventilator prior to said guiding of said endotracheal tube through said LMA; and
   connecting said endotracheal tube to said ventilator following said positioning in the trachea of the patient.

4. The method of claim 3, further comprising disconnecting said ventilator and said visualization device from said endotracheal tube prior to said removing of said LMA.

5. The method of claim 4, wherein said mask portion comprises an LMA cuff, further comprising:
   inflating said LMA cuff following said positioning of said LMA in the patient; and deflating said LMA cuff prior to said removing of said LMA.

6. The method of claim 5, wherein said endotracheal tube comprises a tracheal cuff, the method further comprising:
   inflating said tracheal cuff following said positioning in the trachea of the patient.

7. The method of claim 6, wherein said endotracheal tube comprises a light source, a single ventilation lumen, and a visualization channel formed in a wall of the endotracheal tube and extending longitudinally adjacent the single ventilation lumen, and wherein said visualization device and said light source are positioned in the visualization channel.

8. The method of claim 6, wherein said endotracheal tube comprises a single ventilation lumen, a fluid injection channel formed in a wall of the endotracheal tube and extending longitudinally adjacent the single ventilation lumen, and a nozzle fluidly coupled to the fluid injection channel, wherein said visualization device comprises a lens at a distal end thereof, wherein said endotracheal tube further comprises an injection connector in fluid communication with said nozzle, the method further comprising:
   injecting a fluid through the injection connector to discharge the fluid through the nozzle to clean said lens.

* * * * *